(12) United States Patent
O'Shea et al.

(10) Patent No.: US 6,420,565 B2
(45) Date of Patent: Jul. 16, 2002

(54) PROCESS FOR MAKING 2, 5-SUBSTITUTED PYRIDINE

(75) Inventors: Paul O'Shea, Montreal; Xin Wang, Kirkland, both of (CA); Richard Tillyer, Cranford, NJ (US)

(73) Assignees: Merck & Co., Inc., Rahway, NJ (US); Merck Frosst Canada & Co, Kirkland (CA)

( * ) Notice: Subject to any disclaimer, the term of this patent is extended or adjusted under 35 U.S.C. 154(b) by 0 days.

(21) Appl. No.: 09/795,027

(22) Filed: Feb. 27, 2001

Related U.S. Application Data

(60) Provisional application No. 60/185,630, filed on Feb. 29, 2000.

(51) Int. Cl.$^7$ ............................................. C07D 213/61

(52) U.S. Cl. ........................ 546/345; 546/303; 546/314; 546/344; 546/345

(58) Field of Search ................................. 546/303, 314, 546/344, 345

(56) References Cited

PUBLICATIONS

Wang et al "Selective Monolithiation, etc." Tet Letts, 41 (2000) 4335–4338.*

* cited by examiner

*Primary Examiner*—Patricia L. Morris
(74) *Attorney, Agent, or Firm*—Shu M. Lee; David L. Rose

(57) ABSTRACT

2-lithio-5-halopyridine is formed as a predominant component of a reaction mixture by reacting BuLi with 2,5-dihalopyridine in a non-coordinating solvent.

8 Claims, No Drawings

PROCESS FOR MAKING 2, 5-SUBSTITUTED PYRIDINE

This application claims benefit of provisional application Ser. No. 60/185,630, filed Feb. 29, 2000.

BACKGROUND OF THE INVENTION

1. Field of the Invention

The present invention is directed to a process for making 2,5-substituted pyridine compounds. In particular, this invention is directed to a process for making 2,5-substituted pyridine compounds utilizing butyllithium in order to produce a 2-electrophile 5-halo substituted pyridine.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3',5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms.

Inhibition of PDE4 activity is believed effective for the treatment of osteoporosis by reducing bone loss. For example, Ken-ici Miyamoto et al., Biochem. Pharmacology, 54:613–617(1997) describes the effect of a PDE4 on bone loss. Therefore, it would be desirable to provide novel compounds and compositions that inhibit PDE4 activity.

Novel compounds and compositions that inhibit PDE4 activity remain desirable. Further, more efficient methods to produce known PDE4 inhibiting compounds are a continuing need.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

In many of the processes to produce the compounds described in the above patents and publications, various intermediate compounds are utilized. In particular, 2-electrophile-5-halopyridine intermediate compounds derived from a 2-lithio-5-halopyridine have utility and novel processes to produce such intermediate compounds are desirable.

C. Bolm, et al., Chem. Ber. 125:1169(1992); F. C. Alderweireldt, et al., Nucleosides Nucleotides, 8:891(1989); J. Wicha and M. Masnyl, Heterocycles, 16:521(1981); and F. J. Romero-Salguero and J. M. Lehn, Tetrahedron Lett., 37:2357(1996), describe reactions utilizing coordinating solvents such as ether, MTBE, and THF to cause lithiation at the 5-position, or mixed monolithiation at the 5- and 2-positions, with predominantly lithiation at the 5-lithiated position. M. A. Peterson and J. Mitchell, J.Org.Chem., 62:8237(1997) describes how solvents can influence the formation, structure, and properties of organolithiums. Nevertheless, 2-electrophile-5-halopyridine intermediate compounds derived from a 2-lithio-5-halopyridine are particularly desirable and novel processes to produce such intermediate compounds efficiently are desirable.

SUMMARY OF THE INVENTION

The present invention is directed to a novel method to produce a 2-electrophile-5-halopyridine compound which includes the steps of i) selective monolithiation at the 2 position of 2,5-dihalopyridine with butyllithium to form a 2-lithio-5-halopyridine and ii) replacing the lithio group with an electrophilic group to form the 2-electrophile-5-halopyridine compound.

DETAILED DESCRIPTION OF THE INVENTION

A method of this invention comprises the steps of

A) reacting a compound represented by (I)

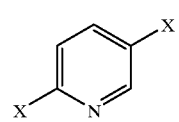

(I)

wherein X is independently bromine or iodine, with an effective amount of BuLi in an effective amount of a non-coordinating solvent at a temperature from about −50° C. to about −78° C. to form a compound represented by (II)

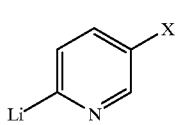

(II)

and

B) reacting (II) with an effective amount of an electrophilic reactant represented by E+ effective to replace the Li with an electrophile represented by E effective to form a compound represented by (III)

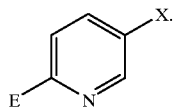

(III)

The halogen, X, is independently iodine or bromine. It is preferred that the halogen is bromine. It is preferred that the compound (I) is 2,5-dibromopyridine.

As used herein, "coordinating solvents" are solvents with oxygen or nitrogen atoms in the solvent molecule. Such solvents are available for coordinating with BuLi or pyridinyl lithium. As used herein, "non-coordinating solvents" are solvents that do not have oxygen or nitrogen atoms for coordination with BuLi or pyridinyl lithium.

As reported in C. Bolm, et al., *Chem. Ber.* 125:1169 (1992); F. C. Alderweireldt, et al., *Nucleosides Nucleotides,* 8:891(1989); J. Wicha and M. Masnyl, *Heterocycles,* 16:521 (1981); and F. J. Romero-Salguero and J. M. Lehn, *Tetrahedron Lett.,* 37:2357(1996), coordinating solvents such as, for example, ether, MTBE, and THF caused lithiation at the 5-position or a mixture of monolithiation at the 5- and 2-positions with predominantly lithiation at the 5-lithiated position.

However, the method of this invention surprisingly found that the use of noncoordinating solvents such as, for example, toluene or methylene chloride produced monolithiation predominantly at the 2-position. Accordingly, this invention forms a reaction product mixture that contains predominantly 2-lithio-5-halopyridine. By predominantly, it is meant that the 2-lithio-5-halopyridine is the largest percent component by weight. Unless specifically stated otherwise, the percentages stated herein are by weight.

EXAMPLES

Comparative Example 1

In Comparative Example 1, following the procedures described in Bolm and the other references above, BuLi (2.5M in hexanes, 1.2 eq.) was added to 0.085M 2,5-dibromopyridine in THF at −78° C. After 40 minutes, the reaction was quenched with 10 mL MeOH and the products were quantified by HPLC. (Zorbax® SB C18, 5 μM, 250× 4.6, 0.1% $H_3PO_4$/CAN 5–96% 12 min hold, 5 min., 2 mL/min., 35° C., 235 nM) The product distribution was found to be 12.3/11.5/66.5/9.8 by weight of 2,5-dilithiopyridine/2-lithio,5-bromopyridine/2-bromo,5-lithiopyridine/2,5-dibromopyridine.

Repeating but quenching after 2 hr, produced a product distribution of 12.3/12.0/65.6/10.1.

Thus, the product was predominantly the 5-lithiated compound.

Comparative Example 2

Comparative Example 2 followed the procedure set forth in Comparative Example 1, except ether was utilized as the solvent. The product distribution, quenching at 40 min., was 4.8/6.9/84.9/3.4. The product distribution, quenching at 2 hr., was 4.3/10.6/81.7/3.4. Finally, the product distribution, quenching after 18 hr., was 8.6/11.3/78.0/2.2.

Thus, the product was predominantly the 5-lithiated compound.

Comparative Example 3

Comparative Example 3 followed the procedure set forth in Comparative Example 2 except that the concentration of the 2,5-dibromopyridine was 0.017M. The product distribution, quenching at 20 min., was 0.3/10.7/44.8/44.4. The product distribution, quenching at 2 hr., was 2.7/27.2/65.7/4.4.

Thus, the product was predominantly the 5-lithiated compound.

Comparative Example 4

Comparative Example 4 followed the procedure set forth in Comparative Example 2 except that the concentration of the 2,5-dibromopyridine was 0.28 M. Although the 2,5-dibromopyridine and its lithiated pyridines were not completely soluble at this concentration, the product distribution, quenching at 40 min., was 9.6/6.7/81.6/2.1. The product distribution, quenching at 160 min., was 10.2/11.2/72.4/6.2. The product distribution, quenching at 4 hr., was 6.5/22.2/59.8/11.5.

Thus, the product was predominantly the 5-lithiated compound.

Comparative Example 5

Comparative Example 5 followed the procedure set forth in Comparative Example 1 except that the solvent used was MTBE (at 0.085M). The product distribution, quenching at 40 min., was 9.6/6.7/81.6/2.1. The product distribution, quenching at 160 min., was 10.2/11.2/72.4/6.2. The product distribution, quenching at 4 hr., was 6.5/22.2/59.8/11.5.

Thus, the product was predominantly the 5-lithiated compound.

Comparative Example 6

Comparative Example 6 followed the procedure set forth in Comparative Example 2 except that the temperature was −50° C. The product distribution, quenching at 40 min., was 15.1/9.1/74.8/1.0. The product distribution, quenching at 2 hr., was 12.8/16.6/69.0/1.6. The product distribution, quenching at 22 hr., was 8.0/40.7/50.2/1.1.

Thus, the product was predominantly the 5-lithiated compound.

Example 1

Example 1 followed the procedure set forth in Comparative Example 1 except that $CH_2Cl_2$ at 0.085M was used at −78° C. The product distribution, quenching at 40 min., was 0.4/83.1/7.9/8.6 while the product distribution, quenching at 2 hr., was 0.7/90.3/8.5/0.6.

Thus, the product was predominantly the 2-lithiated compound.

Example 2

Example 2 followed the procedure set forth in Example 1 except that Toluene at 0.085M was used at −78° C. The product distribution, quenching at 30 min., was 5.2/72.8/4.4/17.7. The product distribution, quenching at 2 hr., was 5.5/83.5/4.2/6.3, while the product distribution, quenching at 3 hr., was 5.0/86.8/4.2/4.0.

Thus, the product was predominantly the 2-lithiated compound.

Example 3

Example 3 followed the procedure set forth in Example 2 except that Toluene at 0.017M was used at −78° C. The product distribution, quenching at 1 hr., was 0.5/67.6/3.0/29.0 while the product distribution, quenching at 7 hr., was 0.6/94.2/2.7/2.5.

Thus, the product was predominantly the 2-lithiated compound.

Example 4

Example 4 followed the procedure set forth in Example 2 except that Toluene at 0.28M was used at −78° C. The product distribution, quenching at 50 min., was 6.7/71.8/11.7/9.8.

Thus, the product was predominantly the 2-lithiated compound.

Example 5

Example 5 followed the procedure set forth in Example 2 except that Toluene at 0.085M was used at −50° C. The product distribution, quenching at 40 min., was 1.5/90.4/7.5/0.5 while the product distribution, quenching at 2 hr., was 1.9/90.2/7.0/0.9.

Thus, the product was predominantly the 2-lithiated compound.

In all cases, 1.2 eq. BuLi were necessary because lithiation using less than 1.2 eq. produced substantial amounts of 2,5-dibromopyridine remaining. The above results from the Comparative Examples 1–6 show that the 2-bromo-5-lithiopyridine is the dominant product for the known processes. The selectivity of the reactions in ether, MTBE, and THF were approximately 12:1, 6.3:1 and 5.8:1 respectively for the 2-bromo-5-lithiopyridine over the 2-lithio-5-bromopyridine. At lower concentration, the selectivity for the 2-bromo-5-lithiopyridine decreased from 12:1 to 4:1. Nevertheless, the reactions would be very inefficient for the production of a substitution by an electrophile at the 2-position of a pyridine analogue.

In comparison, the Examples 1–5, show that the process of this invention produces 2-lithio-5-bromopyridine as the predominant product. For example, after 2 hours reaction time at −78° C., the selectivity of monolithiation in $CH_2Cl_2$ (0.085M) was 11:1 in favor of the 2-position, while in toluene (0.085M) the ratio was 20:1. Dilution also favored the 2-position. For, example, the selectivity for 2-lithio-5-bromopyridine over 2-bromo-5-lithiopyridine reached equilibrium at 34:1 after 7 hours. Furthermore, at this low concentration, only small amounts of 2,5-dilithiopyridine and 2,5-dibromopyridine were detected. Thus, the reactions of this invention were more efficient for the production of a substitution by an electrophile at the 2-position of a pyridine analogue.

Examples 6–13

Following the procedure of Example 2, without quenching, various electrophilic reactants were added to the reaction mixture according to the following schematic formula:

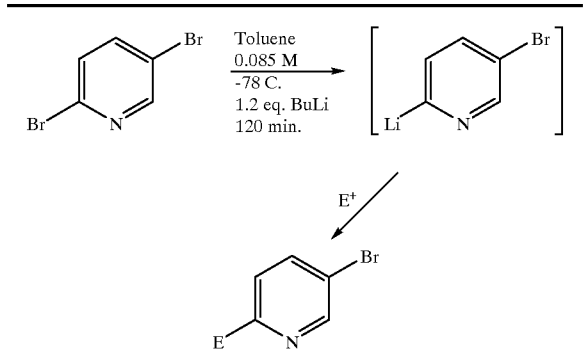

The results are shown in the following table:

| | E+ | E | % Yield | m.p. (° C.) | Lit. m.p. |
|---|---|---|---|---|---|
| Example 6 | DMF | CHO | 49 | 96.4–97.3 | 78–80 |
| Example 7 | DMF/$NaBH_4$ | $CH_2OH$ | 78 | 60.1–60.7 | 52–54 |
| Example 8 | TMSCl | TMS | 51 | Oil | New Cmpd |
| Example 9 | MeSSMe | SMe | 80 | 39.0–39.6 | 38–39 |
| Example 10 | MeSSMe/Oxone | $SO_2Me$ | 77 | 94.7–96.6 | 95–96 |
| Example 11 | PhCOMe | C(OH)MePh | 81 | 69.3–70.8 | New Cmpd |
| Example 12 | $Me_2CO$ | $C(OH)Me_2$ | 79 | Oil | New Cmpd |
| Example 13 | PhCHO | CH(OH)Ph | 82 | Oil | n/a |

The 2-lithio-5-bromopyridine was determined by NMR (toluene-d8, −78° C.): δ6.1–6.2 (m, 2H), 7.8 (s, 1H). In Example 7, in situ treatment of $NaBH_4$ (2 eq.) gave the alcohol directly. In Example 10, in situ treatment of $H_2O$/MeOH/Oxone (3 eq.) gave the sulfone directly. The yields were determined as isolated yields after flash column chromatography. The reference for Examples 6 and 7 was G. Jones, et al., *Tetrahedron,* 53:8257(1997). The reference for Examples 9 and 10 was L. Testaferri, et al., *Tetrahedron,* 41:1373(1996). The reference for Example 13 was Y. Kondo, et al., *J. Chem. Soc. Perkins Trans.,* 1:1781(1996).

A typical procedure is as follows. To a solution of 2,5-dibromopyridine (1.0 g, 4.2 mmol) in toluene (50 mL) at −78° C. was slowly added BuLi (2.5 M in hexanes, 2.0 mL, 5.0 mmol). The reaction mixture was allowed to stand for 2 hr. The electrophilic reactant was then added. The solution was stirred for 1 hr at −78° C. and then warmed to −10° C. $NH_4Cl$ saturated aqueous solution (10 mL) was added and the mixture was warmed to rt. Separation of the two phases gave the toluene solution which was concentrated to dryness. Purification by flash chromatography yielded the desired product.

The results show that the method of this invention can easily and efficiently provide substitution by an electrophile at the 2-position of pyridine while maintaining an accessible halogen substituent at the 5-position of pyridine. Such 2-electrophile-5-halopyridine are useful as intermediate compounds to form PDE4 inhibiting compounds such as

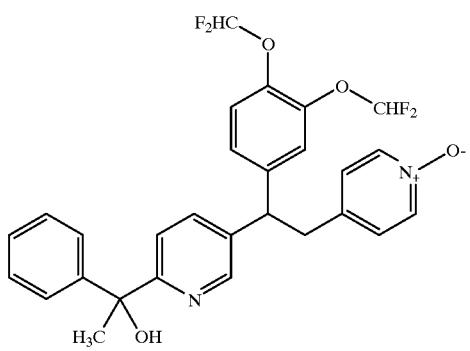

for example.

What is claimed is:

1. A method of forming a reaction product mixture predominantly containing 2-lithio-5-halopyridine, said method comprising the step of:

reacting a compound represented by (I)

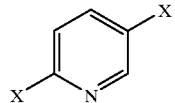

wherein X is independently bromine or iodine, with an effective amount of BuLi in an effective amount of a non-coordinating solvent at a temperature from about −50° C. to about −78° C. to form a compound represented by (II)

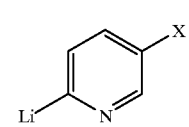

2. The method according to claim 1, wherein said compound represented by (I) is 2,5-dibromopyridine.

3. The method according to claim 1, wherein said non-coordinating solvent is $CH_2Cl_2$ or toluene.

4. A method of forming 2-electrophile-5-halopyridine, said method comprising the steps of A) reacting a compound represented by (I)

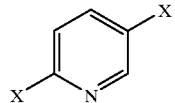

wherein X is independently bromine or iodine, with an effective amount of BuLi in an effective amount of a non-coordinating solvent at a temperature from about −50° C. to about −78° C. to form a reaction product mixture predominantly containing a compound represented by (II)

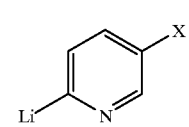

and

B) reacting (II) with an effective amount of an electrophilic reactant represented by E+ effective to replace the Li with an electrophile represented by E effective to form a compound represented by (III)

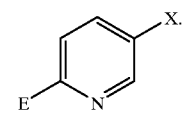

5. The method according to claim 4, wherein said compound represented by (I) is 2,5-dibromopyridine.

6. The method according to claim 4, wherein said non-coordinating solvent is $CH_2Cl_2$ or toluene.

7. The method according to claim 4, wherein said electrophilic reactant is DMF, TMSCl, MeSSMe, PhCOMe, $Me_2CO$, PhCHO, DMF/$NaBH_4$, or MeSSMe/Oxone.

8. The method according to claim 4, wherein said electrophile is CHO, $CH_2OH$, TMS, SMe, $SO_2Me$, C(OH)MePh, C(OH)$Me_2$, or CH(OH)Ph.

* * * * *